US008377878B2

(12) United States Patent
Sampath et al.

(10) Patent No.: US 8,377,878 B2
(45) Date of Patent: *Feb. 19, 2013

(54) THERAPIES FOR CHRONIC RENAL FAILURE

(75) Inventors: Kuber T. Sampath, Holliston, MA (US); Charles M. Cohen, Weston, MA (US); Slobodan Vukicevic, Zagreb (HR)

(73) Assignee: Stryker Corporation, Kalamazoo, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 13/207,584

(22) Filed: Aug. 11, 2011

(65) Prior Publication Data

US 2012/0004171 A1    Jan. 5, 2012

Related U.S. Application Data

(63) Continuation of application No. 12/404,559, filed on Mar. 16, 2009, now Pat. No. 8,017,580, which is a continuation of application No. 11/016,499, filed on Dec. 17, 2004, now Pat. No. 7,524,817, which is a continuation of application No. 08/851,628, filed on May 6, 1997, now Pat. No. 6,861,404, which is a continuation-in-part of application No. 08/643,321, filed on May 6, 1996, now Pat. No. 6,498,142.

(51) Int. Cl.
A61K 38/18   (2006.01)
A61F 2/06    (2006.01)
C07K 14/51   (2006.01)

(52) U.S. Cl. ......... 514/8.8; 514/15.4; 530/350; 623/1.1

(58) Field of Classification Search .................. None
See application file for complete search history.

(56) References Cited

U.S. PATENT DOCUMENTS

| | | | |
|---|---|---|---|
| 4,237,167 A | 12/1980 | Cavazza | |
| 4,627,839 A | 12/1986 | Young | |
| 5,011,691 A | 4/1991 | Oppermann et al. | |
| 5,013,649 A | 5/1991 | Wang et al. | |
| 5,045,452 A | 9/1991 | Spragg et al. | |
| 5,266,683 A | 11/1993 | Oppermann et al. | |
| 5,525,621 A * | 6/1996 | Burt et al. | 514/393 |
| 5,714,511 A | 2/1998 | Saavedra et al. | |
| 5,723,441 A | 3/1998 | Higley et al. | |
| 5,820,589 A | 10/1998 | Torgerson | |
| 5,849,686 A | 12/1998 | Kuberasampath et al. | |
| 5,879,908 A | 3/1999 | Laping et al. | |
| 6,077,823 A * | 6/2000 | Kuberasampath et al. | 514/1.5 |
| 6,120,760 A | 9/2000 | Hotten et al. | |
| 6,194,376 B1 | 2/2001 | Kuberasampath et al. | |
| 6,288,031 B1 | 9/2001 | Kuberasampath et al. | |
| 6,407,060 B1 | 6/2002 | Charette et al. | |
| 6,498,142 B1 | 12/2002 | Sampath et al. | |
| 6,861,404 B1 | 3/2005 | Cohen et al. | |
| 7,056,882 B2 | 6/2006 | Kuberasampath et al. | |
| 7,147,839 B2 * | 12/2006 | Sampath et al. | 424/9.2 |
| 7,196,056 B2 | 3/2007 | Cohen et al. | |
| 7,524,817 B2 | 4/2009 | Cohen et al. | |
| 8,017,580 B2 * | 9/2011 | Cohen et al. | 514/15.4 |

FOREIGN PATENT DOCUMENTS

| | | |
|---|---|---|
| CA | 1128881 | 8/1982 |
| JP | 04-026624 | 1/1992 |
| WO | WO 88/00205 | 1/1988 |
| WO | WO 90/11366 | 10/1990 |
| WO | WO 91/18098 | 11/1991 |
| WO | WO 92/00067 | 1/1992 |
| WO | WO 92/15323 | 9/1992 |
| WO | WO 93/04692 | 3/1993 |
| WO | WO 93/05172 | 3/1993 |
| WO | WO 93/05751 | 4/1993 |
| WO | WO 94/03075 | 2/1994 |
| WO | WO 94/03200 | 2/1994 |
| WO | WO 94/03600 | 2/1994 |
| WO | WO 94/06449 | 3/1994 |
| WO | WO 94/10203 | 5/1994 |
| WO | WO 94/20539 | 9/1994 |
| WO | WO 95/08621 | 3/1995 |
| WO | WO 95/11983 | 5/1995 |
| WO | WO 95/33830 | 12/1995 |
| WO | WO 97/41880 | 11/1997 |
| WO | WO 97/41881 | 11/1997 |

OTHER PUBLICATIONS

Simic et al. Bone morphogenetic proteins in development and homeostasis of kidney. Cytokine Growth Factor Rev. Jun. 2005;16(3):299-308.*

Anderson et al., "Acute renal failure," *Harrison's principles of internal medicine*, 9th ed., Isselbacher et al. (Eds.), Chpt. 275, p. 1293-1299 (New York: McGraw-Hill, 1980).

Asahina et al., "Human osteogenic protein-1 induces both chondroblastic and osteoblastic differentiation of osteoprogenitor cells derived from newborn rat calvaria," *J. Cell. Biol.*, 123(4):921-933 (1993).

Avner, "Polypeptide growth factors in metanephric growth and segmental nephron differentiation," *Pediatr. Nephrol.*, 4:372-377 (1990).

Bard et al., "Towards a genetic basis for kidney development," *Mech. Develop.*, 48:3-11 (1994).

Basic, "The role of bone morphogenetic proteins in renal compensatory growth," LijecnickiVjesnik,HR, Urednistvo Lijecnickog Vjesnika; Zagreb, 119(2):53-55 (1997) ISSN: 0024-3477, CODEN: LIVJA5.

Border et al., "Suppression of experimental glomerulonephritis by antiserum against transforming growth factor β1," *Nature*, 346:371-374 (1990).

Bowie et al., "Deciphering the message in protein sequences: tolerance to amino acid substitutions," *Science*, 247:1306-1310 (1990).

(Continued)

*Primary Examiner* — David Romeo
(74) *Attorney, Agent, or Firm* — Ropes & Gray LLP; James F. Haley, Jr.; Karen Mangasarian

(57) ABSTRACT

The present invention provides methods for the treatment, and pharmaceuticals for use in the treatment, of mammalian subjects in, or at risk of chronic renal failure, or at risk of a need for renal replacement therapy. The methods involve the administration of certain proteins of, or based upon, the osteogenic protein/bone morphogenetic protein (OP/BMP) family within the TGF-β superfamily of proteins.

10 Claims, 6 Drawing Sheets

OTHER PUBLICATIONS

Brady et al., "Acute renal failure," *Harrison's principles of internal medicine*, 13th ed., Isselbacher et al. (Eds.), Chpt. 236, pp. 1265-1274 (New York: McGraw-Hill, 1994).

Brenner et al., "Chronic renal failure," *Harrison's principles of internal medicine*, 13th ed., Isselbacher et al. (Eds.), Chpt. 238, pp. 1274-1281 (New York: McGraw-Hill, 1994).

Carpenter et al., "Dialysis and transplantation in the treatment of renal failure," *Harrison's principles of internal medicine*, 13th ed., Isselbacher et al. (Eds.), Chpt. 238, pp. 1281 (New York: McGraw-Hill, 1994).

Celeste et al., "Identification of transforming growth factor beta family members present in bone-inductive protein purified from bovine bone," *Proc. Natl. Acad. Sci. (USA)*, 87:9843-9847 (1990).

Coe et al., "Approach to the patient with diseases of the kidneys and urinary tract," *Harrison's principles of internal medicine*, 13th ed., Isselbacher et al. (Eds.), Chpt. 237, pp. 1252 (New York: McGraw-Hill, 1994).

Dudley et al., "A requirement for bone morphogenetic protein-7 during development of the mammalian kidney and eye," *Genes & Devel.*, 9:2795-2807 (1995).

Floege et al., "Glomerular cells, extracellular matrix accumulation, and the development of glomerulosclerosis in the remnant kidney model," *Laboratory Investigation*, 66(4):485-497 (1992).

Glassock, "Immunosuppressive treatment in the prevention of renal failure in primary glomerular diseases," *Clin. Exp. Dial. Apheresis*, 5(1-2):21-46 (1981).

Glassock et al., "Immunopathogenic mechanisms of renal injury," *Harrison's principles of internal medicine*, 13th ed., Isselbacher et al. (Eds.), Chpt. 239, pp. 1292-1295 (New York: McGraw-Hill, 1994).

Guler et al., "Effects of recombinant insulin-like growth factor I on insulin secretion and renal function in normal human subjects," *Proc. Natl. Acad. Sci. (USA)*, 86:2868-2872 (1989).

Hamaguchi et al., "Transforming growth factor-$\beta$1 expression and phenotypic modulation in the kidney of hypertensive rats," *Hypertension*, 26(1):199-207 (1995).

Hirschberg et al., "Effects of insulin-like growth factor I on renal function in normal men," *Kidney Intl.* 43:387-397 (1993).

Jennerholm et al., "Magnetic resonance imaging of the transplanted kidney. Correlation to function and histopathology," *Acta Radiologica*, 31(5):499-503 (1990).

Jones et al., "Involvement of bone morphogenetic protein-4 (BMP-4) and Vgr-1 in morphogenesis and neurogenesis in the mouse," *Development*, 111:531-542 (1991).

Kees-Folts et al., "Relationship between hyperlipidemia, lipid mediators, and progressive glomerulosclerosis in the nephrotic syndrome," *Am. J. Nephrol.*, 13(5):365-375 (1993).

Kelly et al., "Intercellular adhesion molecule-1-deficient mice are protected against ischemic renal injury," *J. Clin. Invest.*, 97(4):1056-63 (1996).

Klahr et al., "The progression of renal disease," *N. Eng. J. Med.*, 318(25):1657-1666 (1988).

Kopple, "The rationale for the use of growth hormone or insulin-like growth factor I in adult patients with renal failure," *Miner. Electrolyte Metab.*, 18:269-275 (1992).

Lefer et al., "Anti-ischaemic and endothelial protective actions of recombinant human osteogenic protein (hOP-1)," *J. Mol. Cell. Cardiol.*, 24(6):585-593 (1992).

Lemann et al., "Use of the serum creatinine to estimate glomerular filtration rate in health and early diabetic nephropathy. Collaborative Study Group of Angiotensin Converting Enzyme Inhibition in Diabetic Nephropathy," *Am. J. Kidney Dis.*, 3:236-243 (1990).

Luo et al., "BMP-7 is an inducer of nephrogenesis, and is also required for eye development and skeletal patterning," *Genes & Devel.*, 9:2808-2820 (1995).

Massague, "The transforming growth factor-beta family," *Annu. Rev. Cell Biol.*, 6:597 (1990).

Miller et al., "Effects of IGF-I on renal function in end-stage chronic renal failure," *Kidney Intl.*, 46:201-207 (1994).

Needleman et al., "A general method applicable to the search for similarities in the amino acid sequence of two proteins," *J. Mol. Biol.*, 48:443-453 (1970).

Ngo et al., "Computational complexity, protein structure prediction, and the Levinthal Paradox," *The Protein Folding Problem and Tertiary Structure Prediction*, Merz and Le Grand (Eds) Springer Verlag, 433:492-495 (1994).

Ozkaynak et al., "OP-1 cDNA encodes an osteogenic protein in the TGF-beta family," *EMBO J.*, 9:2085-2093 (1990).

Ozkaynak et al., "Murine osteogenic protein (OP-1): High levels of mRNA in kidney," *Biochem. Biophys. Res. Comm.*, 179(1):116-123 (1991).

Ozkaynak et al., "Osteogenic protein-2: A new member of the transforming growth factor-$\beta$ superfamily expressed early in embryogenesis," *J. Biol. Chem.*, 267(35):25220-25227 (1992).

Ponticelli et al., "Conventional treatment of idiopathic nephrotic syndrome and membranous nephropathy in adults," *Clin. Nephrol.*, 35(S1):S16-S21 (1991).

Samaan et al., "Growth hormone levels in severe renal failure," *Metabolism*, 19(2):102-113 (1970).

Sampath et al., "Dissociative extraction and reconstitution of extracellular matrix components involved in local bone differentiation," *Proc. Natl. Acad. Sci. (USA)*, 78:7599-7603 (1981).

Sampath et al., "Bovine osteogenic protein is composed of dimers of OP-1 and BMP-2A, two members of the transforming growth factor-beta superfamily," *J. Biol. Chem.*, 265:13198-13205 (1990).

Sampath et al., "Recombinant human osteogenic protein-1 (hOP-1) induces new bone formation in vivo with a specific activity comparable with natural bovine osteogenic protein and stimulates osteoblast proliferation and differentiation in vitro," *J. Biol. Chem.*, 267(28):20352-20362 (1992).

Schiller et al., "Focal glomerulosclerosis in the remnant kidney model—an inflammatory disease mediated by cytokines," *Nephrology, Dialysis, Transplantation*, 12(3):430-437 (1997).

Shankland et al., "Expression of transforming growth factor-$\beta$1 during diabetic renal hypertrophy," *Kidney Intl.*, 46:430-442 (1994).

Tamaki et al., "TGF-$\beta$1 in glomerulosclerosis and interstitial fibrosis of adriamycin nephropathy," *Kidney Intl.*, 45:525-536 (1994).

Toback, "Regeneration after acute tubular necrosis," *Kidney Intl.*, 41:226-246 (1992).

Tolins et al., "Mechanisms of hypertensive glomerular injury," *Am. J. Cardiol.*, 62(11):54G-58G (1988).

Vukicevic et al., "Localization of osteogenic protein-1 (Bone Morphogenetic Protein-7) during human embryonic development: High affinity binding to basement membranes," *Biochem. Biophys. Res. Comm.*, 198(2):693-700 (1994).

Vukicevic et al., "Developing human lung and kidney are major sites for synthesis of bone morphogenetic protein-3 (Osteogenin)," *J. Histochem. Cytochem.*, 42(7):869-875 (1994).

Vukicevic et al., "Induction of nephrogenic mesenchyme by osteogenic protein 1 (bone morphogenetic protein 7)," *Proc. Natl. Acad. Sci. (USA)*, 93(17):9021-9026 (1996).

Vukicevic et al., "Recombinant human OP-1 (BMP-7) prevents rapid loss of glomerular function and improves mortality associated with chronic renal failure," *J. Am. Soc. Nephrol.*, 7(9):1867 (1996).

Watanabe et al., "Production of hydrogen peroxide by neutrophilic polymorphonuclear leukocytes in patients with diabetic nephropathy," *J. Clin. Lab. Anal.*, 7(4):209-213 (1993).

Wozney et al., "Novel regulators of bone formation: Molecular clones and activities," *Science*, 242:1528-1534 (1988).

Wright et al., "Serum-growth hormone and glucose intolerance in renal failure," *The Lancet*, 2:798-800 (1968).

Yamamoto et al., "Expression of transforming growth factor $\beta$ is elevated in human and experimental diabetic nephropathy," *Proc. Natl. Acad. Sci. (USA)*, 90:1814-1818 (1993).

Yamamoto et al., "Sustained expression of TGF-$\beta$ underlies development of progressive kidney fibrosis," *Kidney Intl.*, 45:916-927 (1994).

Yang et al., "Local macrophage and myofibroblast proliferation in progressive renal injury in the rat remnant kidney," *Nephrology, Dialysis, Transplantation*, 13(8):1967-1974 (1998).

Creative Biomolecules Inks Deals with Purdue, Stryker—OP-1 a Major Focus, Biotech. Law Report 15(4):616-617 (1996).

Marrus, PR Newswire, Researchers Present First Preclinical Studies Suggesting Op-1 Can Protect Against Acute Renal Failure, Nov. 1996.

Marrus, PR Newswire, Creative Biomolecules' OP-1 Protects Against Kidney Damage in Models of Acute and Chronic Renal Failure, May 1996.

* cited by examiner

```
                        SEQUENCE LISTING

<160> NUMBER OF SEQ ID NOS: 1

<210> SEQ ID NO 1
<211> LENGTH: 431
<212> TYPE: PRT
<213> ORGANISM: Homo sapiens
<220> FEATURE:
<223> OTHER INFORMATION: OP-1

<400> SEQUENCE: 1

Met His Val Arg Ser Leu Arg Ala Ala Pro His Ser Phe Val Ala
 1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
                35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
```

```
                    305                 310                 315                 320
Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
        370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
                420                 425                 430
```

THERAPIES FOR CHRONIC RENAL FAILURE

CROSS-REFERENCE TO RELATED APPLICATIONS

The present application is a continuation of U.S. application Ser. No. 12/404,559, filed Mar. 16, 2009, which is a continuation of U.S. application Ser. No. 11/016,499, filed Dec. 17, 2004 (now U.S. Pat. No. 7,524,817), which is a continuation of U.S. application Ser. No. 08/851,628 filed May 6, 1997 (now U.S. Pat. No. 6,861,404), which is a continuation-in-part of U.S. application Ser. No. 08/643,321, filed May 6, 1996 (now U.S. Pat. No. 6,498,142). The disclosure of each of the above-mentioned applications is incorporated by reference herein.

FIELD OF THE INVENTION

The present invention relates generally to methods of treatment for renal disease. In particular, the invention relates to methods of treatment for conditions which place mammals, including humans, in, or at risk of chronic renal failure. The methods involve the administration of certain proteins of; or based upon, the osteogenic protein/bone morphogenetic protein (OP/BMP) family within the TGF-β super family of proteins.

BACKGROUND OF THE INVENTION

The mammalian renal system serves primary roles both in the removal of catabolic waste products from the bloodstream and in the maintenance of fluid and electrolyte balances in the body. Renal failures are, therefore, life-threatening conditions in which the build-up of catabolites and other toxins, and/or the development of significant imbalances in electrolytes or fluids, may lead to the failure of other major organs systems and death. As a general matter, renal failure is classified as "acute" or "chronic." As detailed below, chronic renal failure is a debilitating and life-threatening disease for which no adequate treatment exists.
Chronic Renal Failure Chronic renal failure may be defined as a progressive, permanent and significant reduction of glomerular filtration rate (GFR) due to a significant and continuing loss of nephrons. Chronic renal failure typically begins from a point at which a chronic renal insufficiency (i.e., a permanent decrease in renal function of at least 50-60%) has resulted from some insult to the renal tissues which has caused a significant loss of nephron units. The initial insult may or may not have been associated with an episode of acute renal failure. Irrespective of the nature of the initial insult, chronic renal failure manifests a "final common path" of signs and symptoms as nephrons are progressively lost and GFR progressively declines. This progressive deterioration in renal function is slow, typically spanning many years or decades in human patients, but seemingly inevitable.

The early stage of chronic renal failure typically begins when GFR has been reduced to approximately one-third of normal (e.g., 30-40 ml/min for an average human adult). As a result of the significant nephron loss, and in an apparent "attempt" to maintain the overall GFR with fewer nephrons, the average single nephron GFR (SNGFR) is increased by adaptations of the remaining nephrons at both the structural and functional level. One structural manifestation of this adaptation, readily detectable by microscopic examination of biopsy samples, is a "compensatory hypertrophy" of both the glomeruli and the tubules of the kidney, a process which literally increases the volume of filtrate which can be produced by each remaining nephron by literal enlargement of the glomeruli and tubules. Indeed, as a result of the hypertrophy or dilation of the collecting ducts, the urine of subjects with chronic renal failure often contains broad "casts," typically 2-6 times normal diameter, which aid in diagnosis and have also been referral to as "renal failure casts." At the same time, there are functional changes in the remaining nephrons, such as decreased absorption or increased secretion of normally excreted solutes, which may be responses to hormonal or paracrine changes elsewhere in the body (e.g., increasing levels of parathyroid hormone (PTH) in response to changes in serum levels of calcium and phosphate).

These adaptations in early stage chronic renal failure are not successful completely restoring GFR or other parameters of renal function and, in fact, subject the remaining nephrons to increased risk of loss. For example, the increased SNGFR is associated with mechanical stresses on the glomerulus due to hypertension and hyper perfusion. The loss of integrity of podocyte junctures leads to increased permeability of the glomerulus to macromolecules or "leakiness" of the glomerular capsule. Proliferative effects are also observed in mesangial, epithelial and endothelial cells, as well as increases in the deposition of collagen and other matrix proteins. Sclerosis of both the glomeruli and tubules is another common symptom of the hypertrophied nephrons and the risk of coagulation in the glomerulus is increased. In particular, these adaptations of the remaining nephrons, by pushing the SNGFR well beyond its normal level, actually decrease the capacity of the remaining nephrons to respond to acute changes in water, solute, or acid loads and, therefore, actually increase the probability of additional nephron loss.

As chronic renal failure progresses, and GFR continues to decline to less than 10% of normal (e.g., 5-10 ml/mm), the subject enters end-stage renal disease (ESRD). During this phase, the inability of the remaining nephrons to adequately remove waste products from the blood, while retaining useful products and maintaining fluid and electrolyte balance, leads to a rapid decline in which many organ systems, and particularly the cardiovascular system, may begin to fail. For example, BUN and creatinine levels may be expected to rise and, at BUN levels of 60-100 mg/dL and serum creatinine levels of 8-12 mg/dL, a uremic syndrome will typically develop in which the kidneys can no longer remove the end products of nitrogen metabolism. At this point, renal failure will rapidly progress to death unless the subject receives renal replacement therapy (i.e., chronic hemodialysis, continuous peritoneal dialysis, or kidney transplantation).

Approximately 600 patients per million receive chronic dialysis each year in the United States, at an average cost approaching $60,000-$80,000 per patient per year. Of the new cases of end-stage renal disease each year, approximately 28-33% are due to diabetic nephropathy (or diabetic glomerulopathy or diabetic renal hypertrophy), 24-29% are due to hypertensive nephrosclerosis (or hypertensive glomerulosclerosis), and 15-22% are due to glomerulonephritis. The 5-year survival rate for all chronic dialysis patients is approximately 40%, but for patients over 65, the rate drops to approximately 20%.

A need remains, therefore, for treatments which will prevent the progressive loss of renal function which has caused almost two hundred thousand patients in the United States alone to become dependent upon chronic dialysis, and which results in the premature deaths of tens of thousands each year.

SUMMARY OF THE INVENTION

The present invention is directed to methods of treatment, and pharmaceutical preparations for use in the treatment, of mammalian subjects in, or at risk chronic renal failure, or at risk of the need for renal replacement therapy. Such subjects include subjects already afflicted with chronic renal failure, or which have already received renal replacement therapy, as well as any subject reasonably expected to suffer a progressive loss of renal function associated with progressive loss of functioning nephron units. Whether a particular subject is at risk is a determination which may routinely be made by one of ordinary skill in the relevant medical or veterinary art. Subjects in, or at risk of, chronic renal failure, or at risk of the need for renal replacement therapy, include but are not limited to the following: subjects which may be regarded as afflicted with chronic renal failure, end-stage renal disease, chronic diabetic nephropathy, hypertensive nephrosclerosis, chronic glomerulonephritis, hereditary nephritis, and/or renal dysplasia; subjects having a biopsy indicating glomerular hypertrophy, tubular hypertrophy, chronic glomerulosclerosis, and/or chronic tubulointerstitial sclerosis; subjects having an ultrasound, MRI, CAT scan, or other non-invasive examination indicating renal fibrosis; subjects having an unusual number of broad casts present in urinary sediment; subjects having a GFR which is chronically less than about 50%, and more particularly less than about 40%, 30% or 20%, of the expected GFR for the subject; human male subjects weighing at least about 50 kg and having a GFR which is chronically less than about 50 ml/min, and more particularly less than about 40 ml/min, 30 ml/min or 20 ml/min; human female subjects weighing at least about 40 kg and having a GFR which is chronically less than about 40 ml/mm, and more particularly less than about 30 ml/min, 20 ml/min or 10 ml/min; subjects possessing a number of functional nephron units which is less than about 50%, and more particularly less than about 40%, 30% or 20%, of the number of functional nephron units possessed by a healthy but otherwise similar subject; subjects which have a single kidney; and subjects which are kidney transplant recipients.

The methods and compositions of this invention capitalize in part upon the discovery that certain proteins of eukaryotic origin, defined herein as renal therapeutic agents, and including members of the osteogenic protein/bone morphogenetic protein (OP/BMP) family of proteins, may be used in the treatment of subjects at risk, as defined herein, of chronic renal failure or the need for renal replacement therapy. Useful renal therapeutic agents include polypeptides, or functional variants of polypeptides, comprising at least the C-terminal six- or seven-cysteine domain of a mammalian protein selected from the group consisting of OP-1, OP-2, OP-3, BMP2, BMP3, BMP4, BMP5, BMP6, BMP9, and proteins which exhibit at least 70% or, more preferably, 75% or 80% amino acid sequence homology with the amino acid sequence of the seven-cysteine domain of human OP-1; and which are (a) capable of inducing chondrogenesis in the Reddi-Sampath ectopic bone assay (Sampath and Reddi (1981), *Proc. Natl. Acad. Sci.* (*USA*) 78:7599-7603) or a substantially equivalent assay, (b) capable of significantly preventing, inhibiting, delaying or alleviating the progressive loss of renal function in a standard animal model of chronic renal failure, or (c) capable of causing a clinically significant improvement in a standard marker of renal function when administered to a mammal in, or at risk of, chronic renal failure.

The renal therapeutic agents of the invention may be administered by any route of administration which is compatible with the selected agent, and may be formulated with any pharmaceutically acceptable carrier appropriate to the route of administration. Preferred routes of administration are parenteral and, in particular, intravenous, intraperitoneal, and renal intracapsular. Treatments are also preferably conducted over an extended period on an outpatient basis. Daily dosages of the renal therapeutic agents are expected to be in the range of about 0.01-1000 µg/kg body weight, and more preferably about 10-300 µg/kg body weight, although precise dosages will vary depending upon the particular renal therapeutic agent employed and the particular subject's medical condition and history.

The treatments of the present invention are useful in preventing, inhibiting or delaying the progressive loss of functional nephron units, and the consequent progressive loss of renal function, which typify chronic renal. As such they are of great value in preventing or delaying the need for chronic dialysis or renal replacement therapy in subjects with chronic renal insufficiency, or reducing the necessary frequency of chronic renal dialysis in subjects with end-stage renal disease. As such, they are useful in prolonging the lives, and in maintaining the quality of life, of subjects at risk of, or already afflicted with, chronic renal failure.

DETAILED DESCRIPTION OF THE INVENTION

I. Definitions

Figure 1:
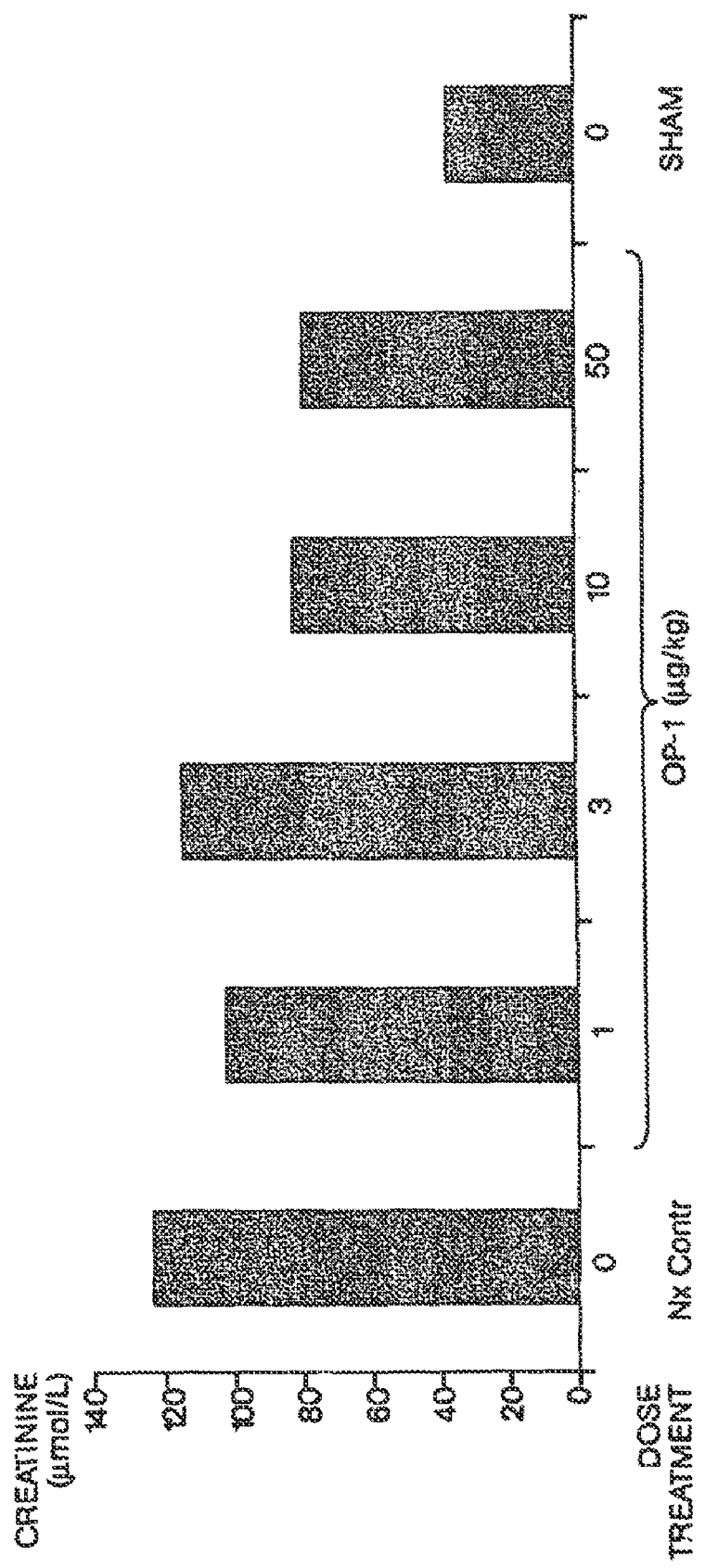
FIG. 1. This figure is a bar graph showing average serum creatinine levels for groups of sham-operated ("SHAM") or partially nephrectomized ("Nx Contr" and "OP-1") rats. 5-6 months post-surgery, rats received injections of vehicle only ("Nx control" and "SHAM") or 1, 3, 10 or 50 µg/kg body weight of soluble OP-1 ("OP-1") three times a week for 4-8 weeks.

In order to more clearly and concisely point out the subject matter of the claimed invention, the following definitions are provided for specific terms used in the following written description and appended claims.

Renal therapeutic agent. As used herein, the term "renal therapeutic agent" means a polypeptide, or a functional variant of a polypeptide, comprising at least the C-terminal six or seven-cysteine domain of a mammalian protein selected from the group consisting of OP-1, OP-2, OP-3, BMP2, BMP3, BMP4, BMP5, BMP6, BMP9, and proteins which exhibit at least 70% or, more preferably, 75% or 80% amino acid sequence homology with the amino acid sequence of the seven-cysteine domain of human OP-1; and which is (a) capable of inducing chondrogenesis in the Reddi-Sampath ectopic bone assay (Sampath and Reddi (1981), Proc. Natl. Acad. Sci. (USA) 78:7599-7603) or a substantially equivalent assay, (b) capable of significantly preventing, inhibiting, delaying or alleviating the progressive loss of renal function in a standard animal model of chronic renal failure, or (c) capable of causing a clinically significant improvement in a standard marker of renal function when administered to a mammal in, or at risk of chronic renal failure. As used herein, a percentage "homology" between two amino acid sequences indicates the percentage of amino acid residues which are identical or similar between the sequences and, as used herein, "similar" residues are "conservative substitutions" which fulfill the criteria defined for an "accepted point mutation" in Dayhoff et al. (1978), *Atlas of Protein Sequence and Structure* Vol. 5 (Suppl. 3), pp. 354-352, Natl. Biomed. Res. Found., Washington, D.C.

Therapeutic efficacy. As used herein, a renal therapeutic agent of the invention is said to have "therapeutic efficacy," and an amount of the agent is said to be "therapeutically effective," if administration of that amount of the agent is sufficient to cause a clinically significant improvement in a standard marker of renal function when administered to a mammalian subject (e.g., a human patient) in, or at risk of, chronic renal failure. Such markers of renal function are well known in the medical literature and include, without being limited to, rates of increase in BUN levels, rates of increase in serum creatinine, static measurements of BUN, static measurements of serum creatinine, glomerular filtration rates (GFR), ratios of BUN/creatinine, serum concentrations of sodium (Na+), urine/plasma ratios for creatinine, urine/plasma ratios for urea, urine osmolality, daily urine output, and the like (see, for example, Brenner and Lazarus (1994), in *Harrison's Principles of Internal Medicine* 13th edition, Isselbacher et al., eds., McGraw Hill Text, New York; Luke and Strom (1994), in *Internal Medicine* 4th Edition, J. H. Stein, ed., Mosby-Year Book, Inc. St. Louis.)

Glomerular Filtration Rate (GFR). The "glomerular filtration rate" or "GFR" is proportional to the rate of clearance into urine of a plasma-borne substance which is not bound by serum proteins, is freely filtered across glomeruli, and is neither secreted nor reabsorbed by the renal tubules. Thus, as used herein, GFR preferably is defined by the following equation:

$$GFR = \frac{U_{conc} \times V}{P_{conc}}$$

where $U_{conc}$ is the urine concentration of the marker, $P_{conc}$ is the plasma concentration of the marker, and V is the urine flow rate in ml/min. Optionally, GFR is corrected for body surface area. Thus, the GFR values used herein may be regarded as being in units of ml/min/1.73 m².

The preferred measure of GFR is the clearance of inulin but, because of the difficulty of measuring the concentrations of this substance, the clearance of creatinine is typically used in clinical settings. For example, for an average size, healthy human male (70 kg, 20-40 yrs), a typical GFR measured by creatinine clearance is expected to be approximately 125 ml/min with plasma concentrations of creatinine of 0.7-1.5 mg/dL. For a comparable, average size woman, a typical GFR measured by creatinine clearance is expected to be approximately 115 ml/min with creatinine levels of 0.5-1.3 mg/dL. During times of good health, human GFR values are relatively stable until about age 40, when GFR typically begins to decrease with age. For subjects surviving to age 85 or 90, GFR may be reduced to 50% of the comparable values at age 40.

Expected Glomerular Filtration Rate ($GFR_{exp}$). An estimate of the "expected GFR" or "$GFR_{exp}$" may be provided based upon considerations of a subject's age, weight, sex, body surface area, and degree of musculature, and the plasma concentration of some marker compound (e.g., creatinine) as determined by a blood test. Thus, as an example, an expected GFR or $GFR_{exp}$ may be estimated as:

$$GFR_{exp} \approx \frac{(140 - \text{age}) \times \text{weight(kg)}}{72 \times P_{conc}(\text{mg/dl})}$$

This estimate does not take into consideration such factors as surface area, degree of musculature, or percentage body fat. Nonetheless, using plasma creatinine levels as the marker, this formula has been employed for human males as an inexpensive means of estimating GFR. Because creatinine is produced by striated muscle, the expected GFR or $GFR_{exp}$ of human female subjects is estimated by the same equation multiplied by 0.85 to account for expected differences in muscle mass, (See Lemann, et al. (1990) *Am. J. Kidney Dis.* 16(3):236-243.)

Broad Cast. Microscopic examination of urinary sediment for the presence of formed elements is a standard procedure in urinalysis. Amongst the formed elements which may be present in urine are cylindrical masses of agglutinated materials that typically represent a mold or "cast" of the lumen of a distal convoluted tubule or collecting tubule. In healthy human subjects, such casts typically have a diameter of 15-25 µm. In subjects with chronic renal failure, however, hypertrophy of the tubules may result in the presence of "broad casts" or "renal failure casts" which are 2-6 times the diameter of normal casts and often have a homogeneous waxy appearance. Thus, as used herein, a "broad cast" means a urinary sediment cast having a diameter of 2-6 times normal, or about 30-150 µm for human casts.

Chronic. As used herein with respect to clinical indications such as urinary casts, measured GFR, or other markers of renal function, "chronic" means persisting for a period of at least three, and more preferably, at least six months. Thus, for example, a subject with a measured GFR chronically below 50% of $GFR_{exp}$ is a subject in which the GFR has been measured and found to be below 50% of $GFR_{exp}$ in at least two measurements separated by at least three, and more preferably, by at least six months, and for which there is no medically sound reason to believe that GFR was substantially (e.g., 10%) higher during the intervening period.

Subjects in, or at risk of, chronic renal failure. As used herein, a subject is said to be in, or at risk of, chronic renal failure, or at risk of the need for renal replacement therapy (i.e., chronic hemodialysis, continuous peritoneal dialysis, or kidney transplantation), if the subject is reasonably expected to suffer a progressive loss of renal function associated with progressive loss of functioning nephron units. Whether a particular subject is in, or at risk of, chronic renal failure is a determination which may routinely be made by one of ordinary skill in the relevant medical or veterinary art. Subjects in, or at risk of, chronic renal failure, or at risk of the need for renal replacement therapy, include but are not limited to the following: subjects which may be regarded as afflicted with chronic renal failure, end-stage renal disease, chronic diabetic nephropathy, hypertensive nephrosclerosis, chronic glomerulonephritis, hereditary nephritis, and/or renal dysplasia; subjects having a biopsy indicating glomerular hypertrophy, tubular hypertrophy, chronic glomerulosclerosis, and/or chronic tubulointerstitial sclerosis; subjects having an ultrasound, MRI, CAT scan, or other non-invasive examination indicating renal fibrosis; subjects having an unusual number of broad casts present in urinary sediment; subjects having a GFR which is chronically less than about 50%, and more particularly less than about 40%, 30% or 20%, of the expected GFR for the subject; human male subjects weighing at least about 50 kg and having a GFR which is chronically less than about 50 ml/min, and more particularly less than about 40 ml/min, 30 ml/min or 20 ml/min; human female subjects weighing at least about 40 kg and having a GFR which is chronically less than about 40 ml/min, and more particularly less than about 30 ml/min, 20 ml/min or 10 ml/min, subjects possessing a number of functional nephron units which is less than about 50%, and more particularly less than about 40%, 30% or 20%, of the number of functional nephron units possessed by a healthy but otherwise similar subject; subjects which have a single kidney; and subjects which are kidney transplant recipients.

II. Description of the Preferred Embodiments

A. General

The present invention depends, in part, upon the surprising discovery that administration of certain protein-based renal therapeutic agents to subjects in, or at risk of chronic renal failure, can reduce mortality and/or morbidity rates, and prevent, inhibit, delay or alleviate the progressive loss of renal function which characterizes chronic renal failure. Alternatively, or in addition, administration of the renal therapeutic agents of the present invention can prevent, inhibit or delay the progressive loss of functional nephron units and the progressive decline in glomerular filtration rate (GFR) which slowly but inevitably leads to the need for renal replacement therapy (i.e., renal transplant or chronic dialysis) or death. In preferred embodiments, the therapeutic agents of the invention are members of the osteogenic protein/bone morphogenetic protein (OP/BMP) family within the TGF-β superfamily of proteins.

B. Renal Therapeutic Agents

The renal therapeutic agents of the present invention are naturally occurring proteins, or functional variants of naturally occurring proteins, in the osteogenic protein/bone morphogenetic protein (OP/BMP) family within the TGF-β superfamily of proteins. That is, these proteins form a distinct subgroup, referred to herein as the "OP/BMP family," within the loose evolutionary grouping of sequence-related proteins known as the TGF-β superfamily. Members of this protein family comprise secreted polypeptides that share common structural features, and that are similarly processed from a pro-protein to yield a carboxy-terminal mature protein. Within the mature protein, all members share a conserved pattern of six or seven cysteine residues defining a 97-106 amino acid domain, and the active form of these proteins is either a disulfide-bonded homodimer of a single family member, or a heterodimer of two different members (see, e.g., Massague (1990), *Annu. Rev. Cell Biol.* 6:597; Sampath et al. (1990), *J. Biol. Chem.* 265:13198). For example, in its mature, native form, natural-sourced human OP-1 is a glycosylated dimer typically having an apparent molecular weight of about 30-36 kDa as determined by SDS-PAGE. When reduced, the 30 kDa protein gives rise to two glycosylated peptide subunits having apparent molecular weights of about 16 kDa and 18 kDa. The unglycosylated protein has an apparent molecular weight of about 27 kDa. When reduced, the 27 kDa protein gives rise to two unglycosylated polypeptide chains, having molecular weights of about 14 kDa to 16 kDa.

Typically, the naturally occurring OP/BMP proteins are translated as a precursor, having an N-terminal signal peptide sequence, a "pro" domain, and a "mature" protein domain. The signal peptide is typically less than 30 residues, and is cleaved rapidly upon translation at a cleavage site that can be predicted using the method of Von Heijne (1986), *Nucleic Acids Research* 14:46834691. The "pro" domain is variable both in sequence and in length, ranging from approximately 200 to over 400 residues. The pro domain is cleaved to yield the "mature" C-terminal domain of approximately 115-180 residues, which includes the conserved six- or seven-cysteine C-terminal domain of 97-106 residues. As used herein, the "pro form" of an OP/BMP family member refers to a protein comprising a folded pair of polypeptides, each comprising a pro domain in either covalent or noncovalent association with the mature domains of the OP/BMP polypeptide. Typically, the pro form of the protein is more soluble than the mature form under physiological conditions. The pro form appears to be the primary form secreted from cultured mammalian cells. The "mature form" of the protein refers to mature C-terminal domain which is not associated, either covalently or noncovalently, with the pro domain. Any preparation of OP-1 is considered to contain mature form when the amount of pro domain in the preparation is no more than 5% of the amount of "mature" C-terminal domain.

OP/BMP family members useful herein include any of the known naturally-occurring native proteins including allele, phylogenetic counterpart and other variants thereof, whether naturally-sourced or biosynthetically produced (e.g., including "muteins" or "mutant proteins"), as well as new, active members of the OP/BMP family of proteins.

Particularly useful sequences include those comprising the C-terminal seven cysteine domains of mammalian, preferably human, human OP-1, OP-2, OP-3, BMP2, BMP3, BMP4, BMP5, BMP6, BMP8 and BMP9. Other proteins useful in the practice of the invention include active forms of GDF-5, GDF-6, GDF-7, DPP, Vg1, Vgr-1, 60A, GDF4, GDF-3, GDF-5, GDF-6, GDF-7, BMP10, BMP11, BMP13, BMP15, UNIVIN, NODAL, SCREW, ADMP or NURAL and amino acid sequence variants thereof. In one currently preferred embodiment, the renal therapeutic agents of the invention are selected from any one of OP-1, OP-2, OP-3, BMP2, BMP3, BMP4, BMP5, BMP6, and BMP9.

Publications disclosing these sequences, as well as their chemical and physical properties, include: OP-1 and OP-2: U.S. Pat. No. 5,011,691, U.S. Pat. No. 5,266,683, and Ozkaynak et at (1990), *EMBO J.* 9:2085-2093; OP-3: WO94/10203; BMP2, BMP3, and BMP4: U.S. Pat. No. 5,013,649, WO91/18098, WO88/00205, and Wozaey et at (1988), *Science* 242:1528-1534; BMP5 and BMP6: WO90/11366 and Celeste et al. (1991), *Proc. Natl. Acad. Sci. (USA)* 87:9843-9847; Vgr-1: Lyons et at (1989), *Proc. Natl. Acad. Sci. (USA)* 86: 4554-4558; DPP: Padgett et al. (1987), *Nature* 325:81-84; Vg1: Weeks (1987), *Cell* 51:861-867; BMP-9: WO95/33830; BMP10: WO94/26893; BMP-11: WO94/26892; BMP12: WO95/16035; BMP-13: WO95/16035; GDF-1: WO92/00382 and Lee et at (1991), *Proc. Natl. Acad. Sci. (USA)* 88:4250-4254; GDF-8: WO94/21681; GDF-9: WO94/

15966; GDF-10: WO95/10539; GDF-11: WO96/01845; BMP-15: WO96/36710; MP121: WO96/01316; GDF-5 (CDMF-1, MP52): WO94/15949, WO96/14335, WO93/16099 and Storm et at (1994); *Nature* 368:639-643; GDF-6 (CDMP-2, BMP13): WO95/01801, WO96/14335 and WO95/10635; GDF-7 (CDMP-3, BMP12): WO95/10802 and WO95/10635; BMP-3b: Takao, et at (1996), *Biochem. Biophys. Res. Comm.* 219:656-662; GDF-3: WO94/15965; 60A: Blaster et at (1993), *Cell* 73:687-702 and GenBank accession number L12032. In another embodiment, useful proteins include biologically active biosynthetic constructs, including novel biosynthetic proteins and chimeric proteins designed using sequences from two or more known OP/BMP family proteins. See also the biosynthetic constructs disclosed in U.S. Pat. No. 5,011,691, the disclosure of which is incorporated herein by reference (e.g., COP-1, COP-3, COP-4, COP-5, COP-7, and COP-16).

In other preferred embodiments, the renal therapeutic agents useful herein include therapeutically effective proteins in which the amino acid sequences comprise a sequence sharing at least 70% amino acid sequence "homology" and, preferably, 75% or 80% homology with the C-terminal seven cysteine domain present in the active forms of human OP-1 (i.e., residues 330-431, as shown in SEQ ID NO: 2 of U.S. Pat. No. 5,266,683). In other preferred embodiments, the renal therapeutic agents useful herein include therapeutically effective proteins in which the amino acid sequences comprise a sequence sharing at least 60% amino acid sequence identity and, preferably, 65% or 70% identity with the C-terminal seven cysteine domain present in the active forms of human OP-1. Thus, a candidate amino add sequence thought to have therapeutic efficacy in the present invention can be aligned with the amino acid sequence of the C-terminal seven cysteine domain of human OP-1 using the method of Needleman et al. (1970), *J. Mol. Biol.* 48:443-453, implemented conveniently by computer programs such as the Align program (DNAstar, Inc.). As will be understood by those skilled in the art, homologous or functionally equivalent sequences include functionally equivalent arrangements of the cysteine residues within the conserved cysteine skeleton, including amino acid insertions or deletions which alter the linear arrangement of these cysteines; but do not materially impair their relationship in the folded structure of the dimeric protein, including their ability to form such intra- or inter-chain disulfide bonds as may be necessary for biological activity. Therefore, internal gaps and amino acid insertions in the candidate sequence are ignored for purposes of calculating the level of amino acid sequence homology or identity between the candidate and reference sequences.

"Amino acid sequence homology" is understood herein to include both amino acid sequence identity and similarity. Thus, as used herein, a percentage "homology" between two amino acid sequences indicates the percentage of amino acid residues which are identical or similar between the sequences. "Similar" residues are "conservative substitutions" which fulfill the criteria defined for an "accepted point mutation" in Dayhoff et at (1978), *Atlas of Protein Sequence and Structure* Vol. 5 (Suppl. 3), pp. 354-352, Natl. Biomed. Res. Found., Washington, D.C. Thus, "conservative substitutions" are residues that are physically or functionally similar to the corresponding reference residues, having similar size, shape, electric charge, and/or chemical properties such as the ability to form covalent or hydrogen bonds, or the like. Examples of conservative substitutions include the substitution of one amino acid for another with similar characteristics, e.g., substitutions within the following groups: (a) valine, glycine; (b) glycine, alanine; (c) valine, isoleucine, leucine; (d) aspartic acid, glutamic acid; (e) asparagine, glutamine; (f) scrim, threonine; (g) lysine, arginine, methionine; and (h) phenylalanine, tyrosine. The term "conservative substitution" or "conservative variation" also includes the use of a substituted amino acid in place of an unsubstituted parent amino acid in a given polypeptide chain, provided that the resulting substituted polypeptide chain also his therapeutic efficacy in the present invention.

The renal therapeutic agents of the invention are also characterized by biological activities which may be readily ascertained by those of ordinary skill in the art. Specifically, a renal therapeutic agent of present invention is (a) capable of inducing chondrogenesis in the Reddi-Sampath ectopic bone assay (Sampath and Reddi (1981), Proc. Natl. Acad. Sci. (USA) 78:7599-7603) or a substantially equivalent assay, (b) capable of significantly preventing, inhibiting, delaying or alleviating the progressive loss of renal function in a standard animal model of chronic renal failure, or (c) capable of causing a clinically significant improvement in a standard marker of renal function when administered to a mammal in, or at risk of chronic renal failure.

The Reddi-Sampath ectopic bone assay is well known in the art as an assay of chondrogenic activity. The assay, which can be easily performed, is described and discussed in, for example, Sampath and Reddi. (1981), *Proc. Natl. Acad. Sci. (USA)* 78:7599-7603; and Wozney (1989), "Bone Morphogenetic Proteins," *Progress in Growth Factor Research* 1:267-280. Many equivalent assays, using other animals and tissue sites, may be employed or developed by those of skill in the art to evaluate the biological activity of the renal therapeutic agents of the present invention. See, for example, the bioassays described in U.S. Pat. No. 5,226,683.

The renal therapeutic agents of the present invention also may be tested in animal models of chronic renal failure. Mammalian models of chronic renal failure in, for example, mice, rats, guinea pigs, cats, dogs, sheep, goats, pigs, cows, horses, and non-human primates, may be created by causing an appropriate direct or indirect injury or insult to the renal tissues of the animal. Animal models of chronic renal failure may, for example, be created by performing a partial (e.g., 5/6) nephrectomy which reduces the number of functioning nephron units to a level which initiates compensatory renal hypertrophy, further nephron lots, and the progressive decline in renal function which characterizes chronic renal failure.

Finally, the renal therapeutic agents of the present invention may be evaluated for their therapeutic efficacy in causing a clinically significant improvement in a standard marker of renal function when administered to a mammalian subject (e.g., a human patient) in, or at risk chronic renal failure. Such markers of renal function are well known in the medical literature and include, without being limited to, rates of increase in BUN levels, rates of increase in serum creatinine, static measurements of BUN, static measurements of serum creatinine, glomerular filtration rates (GFR), ratios of BUN/creatinine, serum concentrations of sodium (Na+), urine/plasma ratios for creatinine, urine/plasma ratios for urea, urine osmolality, daily urine output, and the like (see, for example, Brenner and Lazarus (1994), in *Harrison's Principles of Internal Medicine* 13th edition, Isselbacher et al., eds., McGraw Hill Text, New York; Luke and Strom (1994), in *Internal Medicine,* 4th Edition, J. H. Stein, ed., Mosby-Year Book, Inc. St. Louis.)

The renal therapeutic agents contemplated herein can be expressed from intact or truncated genomic or cDNA or from synthetic DNAs in prokaryotic or eukaryotic host cells. The dimeric proteins can be isolated from the culture media and/or refolded and dimerized in vitro to form biologically active compositions. Heterodimers can be formed in vitro by combining separate, distinct polypeptide chains. Alternatively, heterodimers can be formed in a single cell by co-expressing nucleic acids encoding separate, distinct polypeptide chains. See, for example, WO93/09229, or U.S. Pat. No. 5,411,941, for several exemplary recombinant heterodimer protein production protocols. Currently preferred host cells include, without limitation, prokaryotes including *E. coli*, or eukaryotes including yeast, *Saccharomyces*, insect cells, or mammalian cells, such as CHO, COS or BSC cells. One of ordinary skill in the art will appreciate that other host cells can be used to advantage. Detailed descriptions of the proteins useful in the practice of this invention, including how to make, use and test them for chondrogenic activity, are disclosed in numerous publications, including U.S. Pat. Nos. 5,266,683 and 5,011,691, the disclosures of which are herein incorporated by reference.

C. Subjects for Treatment

As a general matter, the methods of the present invention may be utilized for any mammalian subject in, or at risk of, chronic renal failure, or at risk of the need for renal replacement therapy (i.e., chronic dialysis or renal transplant). Mammalian subjects which may be treated according to the methods of the invention include, but are not limited to, human subjects or patients. In addition, however, the invention may be employed in the treatment of domesticated mammals which are maintained as human companions (e.g., dogs, cats, horses), which have significant commercial value (e.g., dairy cows, beef cattle, sporting animals), which have significant scientific value (e.g., captive or free specimens of endangered species), or which otherwise have value. In addition, as a general matter, the subjects for treatment with the methods of the present invention need not present indications for treatment with the renal therapeutic agents of the invention other than those indications associated with risk of chronic renal failure. That is, the subjects for treatment are expected to be otherwise free of indications for treatment with the renal therapeutic agents of the invention. In some number of cases, however, the subjects may present with other symptoms (e.g., osteodystrophy) for which treatment with the agents of the present invention would be indicated. In such cases, the treatment should be adjusted accordingly so to avoid excessive dosing.

One of ordinary skill in the medical or veterinary arts is trained to recognize subjects which may be at a substantial risk of chronic renal failure, or at substantial risk of the need for renal replacement therapy. In particular, clinical and nonclinical trials, as well as accumulated experience, relating to the presently disclosed and other methods of treatment, are expected to inform the skilled practitioner in deciding whether a given subject is in, or at risk of, chronic renal failure, or at risk of needing renal replacement therapy, and whether any particular treatment is best suited to the subject's needs, including treatment according to the present invention.

As a general matter, a mammalian subject may be regarded as being in, or at risk of, chronic renal failure, or at risk of needing renal replacement therapy, if that subject has already been diagnosed as afflicted with, or would be regarded as being afflicted with, a condition which typically leads to progressive loss of renal function associated with progressive loss of functioning nephron units. Such conditions include, but are not limited to, chronic renal failure, end-stage renal disease, chronic diabetic nephropathy, hypertensive nephrosclerosis, chronic glomerulonephritis, hereditary nephritis, renal dysplasia and the like. These, and other diseases and conditions known in the art, typically lead to a progressive loss of functioning nephrons and to the onset of chronic renal failure.

Frequently, one of skill in the medical or veterinary arts may base a prognosis, diagnosis or treatment decision upon an examination of a renal biopsy sample. Such biopsies provide a wealth of information useful in diagnosing disorders of the kidney but, due to the invasiveness of the procedure, and the additional trauma to a presumably unhealthy kidney, may not be appropriate for all subjects. Nonetheless, subjects in, or at risk of chronic renal failure, or at risk of needing renal replacement therapy, may be recognized by histological indications from renal biopsies including, but not limited to, glomerular hypertrophy, tubular hypertrophy, glomerulosclerosis, tubulointerstitial sclerosis, and the like.

Less invasive techniques for assessing kidney morphology include MRI, CAT and ultrasound scans. Scanning techniques are also available which employ contrasting or imaging agents (e.g., radioactive dyes) but, it should be noted, some of these are particularly toxic to renal tissues and structures and, therefore, their use may be ill-advised in subjects in, or at risk of chronic renal failure. Such non-invasive scanning techniques may be employed to detect conditions such as renal fibrosis or sclerosis, focal renal necrosis, renal cysts, and renal gross hypertrophy which will place a subject in, or at risk of, chronic renal failure, or at risk of needing renal replacement therapy.

Quite frequently, prognosis, diagnosis and/or treatment decisions are based upon clinical indications of renal function. One such indication is the presence in urinary sediment of an unusual number of "broad" or "renal failure" casts, which is indicative of tubular hypertrophy and suggests the compensatory renal hypertrophy which typifies chronic renal failure. A better indication of renal function is the glomerular flow rate (GFR), which can be measured directly by quantifying the rate of clearance of particular markers, or which may be inferred from indirect measurements.

It should be noted that the present invention is not directed to the measurement of GFR or to the diagnosis, of chronic renal failure. The methods of treatment of the present invention need not, therefore, be restricted to subjects presenting with any particular measures of GFR, or any other particular marker of renal function. Indeed, it is not necessary that the GFR of a subject, or any other particular marker of renal function, be determined before practicing the treatments of the present invention. Nonetheless, the measurement of GFR is considered to be a preferred means of assessing renal function.

As is well known in the art, GFR reflects the rate of clearance of a reference or marker compound from the plasma to the urine. The marker compound to be considered is typically one which is freely filtered by the glomeruli, but which is not actively secreted or reabsorbed by the renal tubules, and which is not significantly bound by circulating proteins. The rate of clearance is typically defined by the formula, presented above, which relates the volume of urine produced in a twenty-four period, and the relative concentrations of the marker in the trine and plasma. To be more accurate, the GFR should also be corrected for body surface area. The "gold standard" reference compound is inulin because of its filtration properties and lack of serum-binding. The concentration of this compound is, however, difficult to quantify in blood or urine. The clearance rates of other compounds, including p-aminohippurate (PAH) and creatinine, are therefore often used instead of inulin. In addition, various formulas are often employed which seek to simplify the estimation of actual GFR by omitting considerations of actual urine concentrations of the marker, actual daily volumes of urine produced, or actual body surface area. These values may be replaced by estimates based on other factors, by baseline values established for the same subject, or by standard values for similar subjects. These estimates should be used with caution, however, as they may entail inappropriate assumptions based upon the renal function of normal or healthy subjects.

Various, methods and formulas have been developed in the art which describe an expected value of GFR for a healthy subject with certain characteristics. In particular, formulas are available which provide an expected value of the GFR based upon plasma creatinine levels, age, weight and sex. One such formula for an expected GFR is presented above. Other formulas may, of course, be employed and tables of standard values may be produced for subjects of a given age, weight, sex, and/or plasma creatinine concentration. Newer methods of measuring or estimating GFR (e.g., using NMR or MRI technologies) are also now available in the art and may be used in accordance with the present invention (see, e.g., U.S. Pat. Nos. 5,100,646 and 5,335,660).

As a general matter, irrespective of the manner in which GFR is measured or estimated, a subject may be considered to be in, or at risk of, chronic renal failure, or at risk of needing renal replacement therapy, when the subject has a GFR which is chronically less than about 50% of the expected GFR for that subject. The risk is considered greater as the GFR falls lower. Thus, a subject is increasingly considered at risk if the subject has a GFR which is chronically, less than about 40%, 30% or 20% of the expected GFR.

As a general matter, irrespective of the manner in which GFR is measured or estimated, a human male subject weighing at least about 50 kg may be considered to be in, or at risk of, chronic renal failure, or at risk of needing renal replacement therapy, when the subject has a GFR which is chronically less than about 50 ml/min. The risk is considered greater as the GFR falls lower. Thus, a subject is increasingly considered at risk if the subject has a GFR which is chronically less than about 40, 30 or 20 ml/min.

As a general matter, irrespective of the manner in which GFR is measured or estimated, a human female subject weighing at least about 40 kg may be considered to be in, or at risk of, chronic renal failure, or at risk of needing renal replacement therapy, when the subject has a GFR which is chronically less than about 40 ml/min. The risk is considered greater as the GFR falls lower. Thus, a subject is increasingly considered at risk if the subject has a GFR which is chronically less than about 30, 20 or 10 ml/min.

By a employing a variety of methods, including the histological examinations, non-invasive scanning procedures, evaluations of clinical indicators, and other techniques described above and known in the art, those in the medical and veterinary arts may provide estimates of either the number of functioning nephron units which a subject possesses, or the percentage of functioning nephron units which a subject possesses relative to a healthy but otherwise similar subject (e.g., a conspecific subject of approximately the same age, weight, and sex). Thus, for example, a biopsy may reveal a decrease in the density of functional nephrons, or imaging with filtered agents may indicate losses of functional renal tissue and/or filtering capacity. Such measures or estimates provide another means of expressing when a subject is in, or at risk of, chronic renal failure, or at risk of needing renal replacement therapy. Thus, as a general matter, a subject may be regarded to be in, or at risk of, chronic renal, failure, or at risk of needing renal replacement therapy, if that subject possesses a number of functional nephron units which is less than about 50% of the number of functional nephron units of a healthy, but otherwise similar, subject. As above, the risk is considered greater as the number of functional nephrons decreases further. Thus, a subject is increasingly considered at risk if the subject has a number of functional nephrons which is less than about 40, 30 or 20% of the number for a similar but healthy subject.

Finally, it should be noted that subjects possessing a single kidney, irrespective of the manner of loss of the other kidney (e.g., physical trauma, surgical removal, birth defect), may be considered to be prima facie at risk of chronic renal failure, or the need for renal replacement therapy. This is particularly true for those subjects in which one kidney has been lost due to a disease or condition which may afflict the remaining kidney. Similarly, subjects which are already recipients of a renal transplant, or which are already receiving chronic dialysis (e.g., chronic hemodialysis or continuous ambulatory peritoneal dialysis) may be considered prima facie to be at risk of chronic renal failure, or the need for further renal replacement therapy.

D. Formulations and Methods of Treatment

The renal therapeutic agents of the present invention may be administered by any route which is compatible with the particular renal therapeutic agent employed. Thus, as appropriate, administration may be oral or parenteral, including intravenous, intraperitoneal, and renal intracapsular routes of administration. In addition, administration may be by periodic injections of a bolus of the renal therapeutic agent, or may be made more continuous by intravenous or intraperitoneal administration from a reservoir which is external (e.g., an i.v. bag) or internal (e.g., a bioerodable implant or implanted pump).

The renal therapeutic agents of the invention may be provided to an individual by any suitable means, preferably directly (e.g., locally, as by injection or topical administration to a tissue locus) or systemically (e.g., parenterally or orally). Where the agent is to be provided parenterally, such as by intravenous, subcutaneous, or intramuscular, administration, the agent preferably comprises part of an aqueous solution. The solution is physiologically acceptable so that in addition to delivery of the desired agent to the subject, the solution does not otherwise adversely affect the subjects electrolyte and/or volume balance. The aqueous medium for the agent thus may comprise normal physiologic saline (e.g., 9.85% NaCl, 0.15M, pH 7-7.4).

If desired, a given renal therapeutic agent or other agent may be made more soluble by association with a suitable molecule. For example, association of a mature OP/BMP dimer with an OP/BMP pro domain results in the pro form of the renal therapeutic agent which typically is more soluble or dispersible in physiological solutions than the corresponding mature form. In fact, endogenous members of the OP/BMP family are thought to be transported (e.g., secreted and circulated) in the mammalian body in this form. This soluble form of the protein can be obtained from culture medium of OP/BMP-secreting mammalian cells, e.g., cells transfected with nucleic acid encoding and competent to express the protein. Alternatively, a soluble species can be formulated by complexing the mature dimer (or an active fragment thereof) with a pro domain or a solubility-enhancing fragment thereof (described more fully below). Another molecule capable of enhancing solubility and particularly useful for oral administrations, is casein. For example, addition of 0.2% casein increases solubility of the mature active form of OP-1 by 80%. Other components found in milk and/or various serum proteins also may be useful.

Useful solutions for parenteral administration may be prepared by any of the methods well known in the pharmaceutical art, described, for example, in *Remington's Pharmaceutical Sciences* (Gennaro, A., ed.), Mack Pub., 1990.

Alternatively, the agents described herein may be administered orally. Oral administration of proteins as therapeutics generally is not practiced as most proteins are readily degraded by digestive enzymes and acids in the mammalian digestive system before they can be absorbed into the bloodstream. However, the renal therapeutic exits described herein typically are acid stable and protease resistant (see, for example, U.S. Pat. No. 4,968,590). In addition, at least one of these renal therapeutic agents, OP-1, has been identified in mammary gland extract, colostrum and 57-day milk. Moreover, the OP-1 purified from mammary gland extract is therapeutically efficacious and also is detected in the bloodstream. Finally, soluble form OP-1, e.g., mature OP-1 associated with the pro domain, is therapeutically efficacious. These findings, as well as those disclosed in the examples below, indicate that oral and parenteral administration are viable means for administering the renal therapeutic agents of the invention to an individual. In addition, while the mature forms of certain renal therapeutic agents described herein typically are sparingly soluble, the form found in milk (and mammary gland extract and colostrum) is readily soluble, probably by association of the mature, therapeutically efficacious form with part or all of the pro domain of the intact sequence and/or by association with one or more milk components. Accordingly, the compounds provided herein also may be associated with molecules capable of enhancing their solubility in vitae, or in vivo.

The compounds provided herein also may be associated with molecules capable of targeting the renal therapeutic agent to the desired tissue. For example, an antibody, antibody fragment, or other binding protein that interacts specifically with a surface molecule on cells of the desired tissue, may be used. Useful targeting molecules may be designed, for example, using the single chain binding site technology disclosed, for example, in U.S. Pat. No. 5,091,513.

As will be appreciated by one of ordinary skill in the art, the formulated compositions contain therapeutically effective amounts of the renal therapeutic agent. That is, they contain amounts which provide appropriate concentrations of the agent to the renal tissues for a time sufficient to prevent, inhibit, delay or alleviate permanent or progressive loss of renal function, or otherwise provide therapeutic efficacy. As will be appreciated by those skilled in the art, the concentration of the compounds described in a therapeutic composition of the present invention will vary depending upon a number of factors, including the biological efficacy of the selected agent, the chemical characteristics (e.g., hydrophobicity) of the compounds employed, the formulation of the compound excipients, the administration route, and the treatment envisioned, including whether the active ingredient will be administered directly into a kidney or renal capsule, or whether it will be administered systemically. The preferred dosage to be administered also is likely to depend on such variables such as the condition of the renal tissues, extent of renal function loss, and the overall health status of the particular subject. Dosages may be administered continuously, or daily, but it is currently preferred that dosages be administered once, twice or three firms per week for as long as satisfactory response persists (as measured, for example, by stabilization and/or improvement of renal function by appropriate medical markers and/or quality of life indices) Less frequent dosages, for example monthly dosages, may also be employed. For subjects which would otherwise require continuous, biweekly or tri-weekly hemodialysis sessions, continuous, bi-weekly or tri-weekly intravenous or intraperitoneal infusions are not considered unduly inconvenient. In addition, in order to facilitate frequent infusions, implantation of a semi-permanent stent (e.g., intravenous, intraperitoneal or intracapsular) may be advisable.

The renal therapeutic agents of the invention may, of course, be administered alone or in combination with other molecules known to be beneficial in the treatment of the conditions described herein. When used in combination with other agents, it may be advisable to alter the dosages of the renal therapeutic agents of the present invention accordingly.

Practice of the invention, including additional preferred aspects and embodiments thereof, will be still more fully understood from the following examples, which are presented herein for illustration only and should not be construed as limiting the invention in any way.

Examples

Rat Remnant Kidney Model

A rat partial (5/6) nephrectomy or rat remnant kidney model (RRKM) model was employed essentially as described (Vukicevic, et al, (1987) *J. Bone Mineral Res.* 2:533). Male rats (2-3 months old, weighing about 150-200 g) were subjected to unilateral nephrectomy (either left or right kidney). After approximately one week, ⅔ of the remaining kidney was surgically removed. Immediately following surgery, plasma creatinine and BUN levels rise dramatically due to the loss of renal mass and function. Over the next several weeks of this "acute" failure phase, plasma creatinine and BUN levels of surviving animals decline somewhat toward normal values but remain elevated. Renal function then appears to remain relatively constant or stable for a period of variable duration. After this point, the animals enter a period of chronic renal failure in which there is an essentially linear decline in renal function ending in death.

As surgical controls, additional rats were subjected to a "sham" operation in which the kidneys were decapsulated but no renal tissue was removed.

Intervention Model for Chronic Renal Failure

In this model, both nephrectomized and sham-operated rats were maintained for approximately 5-6 months alter surgery. At this point, surviving nephrectomized animals were past the stable phase and had entered chronic renal failure.

Rats were divided into 8 groups with 12 rats in each group. Two groups of nephrectomized rats were used as controls (Nx controls), with one of those groups receiving no treatment at all, while the other received injections of only the vehicle buffer. In addition, two groups of sham-operated rats were used as controls (sham controls), with one group receiving only the vehicle buffer, while the other received soluble OP-1 (sOP-1) at 10 μg/kg body weight. Four experimental groups of nephrectomized rats were employed, receiving sOP4 at 1, 3, 10 or 50 μg/kg body weight by intraperitoneal injection (OP-1 Nx animals). OP-1 treated and vehicle-only rats received three injections per week for 4-8 weeks. Total injection volume was 300 μl. No statistically significant differences were observed between the two Nx control groups or between the two sham control groups.

Figure 2:
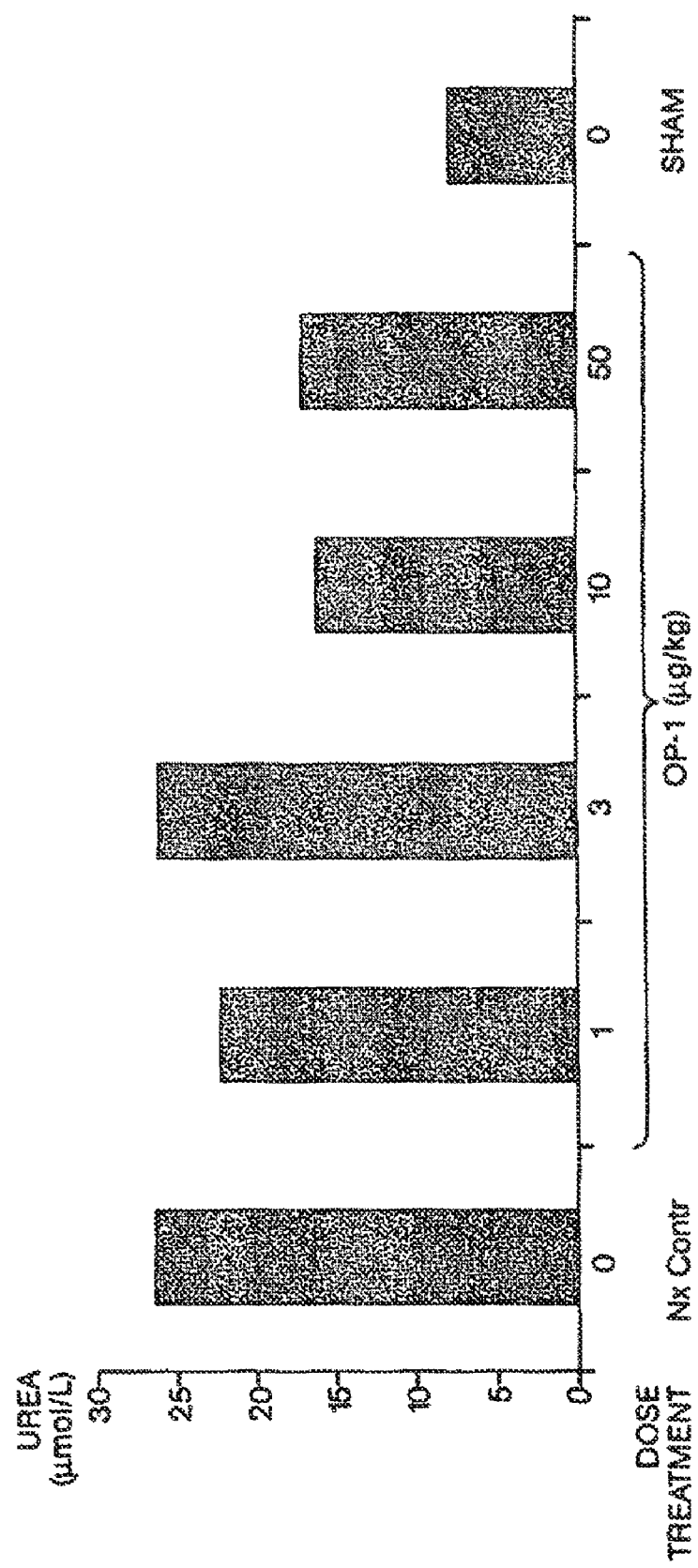
FIG. 2. This figure is a bar graph showing average serum urea levels for groups of sham-operated ("SHAM") or partially nephrectomized ("Nx Contr" and "OP-1") rats. 5-6 months post-surgery, rats received injections of vehicle only ("Nx control" and "SHAM") or 1, 3, 10 or 50 µg/kg body weight of soluble OP-1 ("OP-1") three times a week for 4-8 weeks.

Compared to the sham group receiving only vehicle, the Nx control receiving only vehicle demonstrated significantly ($p<0.01$) elevated serum creatinine (FIG. 1) at the end of the study, indicating a significant loss of renal function. Although nephrectomized rats treated with either 1 or 3 μg/kg body weight sOP-1, did not show significantly reduced serum creatinine when compared to the Nx control, nephrectomized rats treated with sOP-1 at doses of 10 or 50 μg/kg body weight showed significant ($p<0.05$) reductions in creatinine values (FIG. 1). Similar results were observed for serum urea levels: Although nephrectomized rats treated with either 1 or 3 μg/kg body weight sOP-1 did not show significantly reduced serum urea when compared to the Nx control, nephrectomized rats treated with sOP-1 at doses of 10 or 50 μg/kg body weight showed significant ($p<0.01$) reductions in serum urea values (FIG. 2). All nephrectomized rats showed significantly ($p<0.01$) higher serum urea when compared to the sham-operated rats (FIG. 2).

Figure 3C:
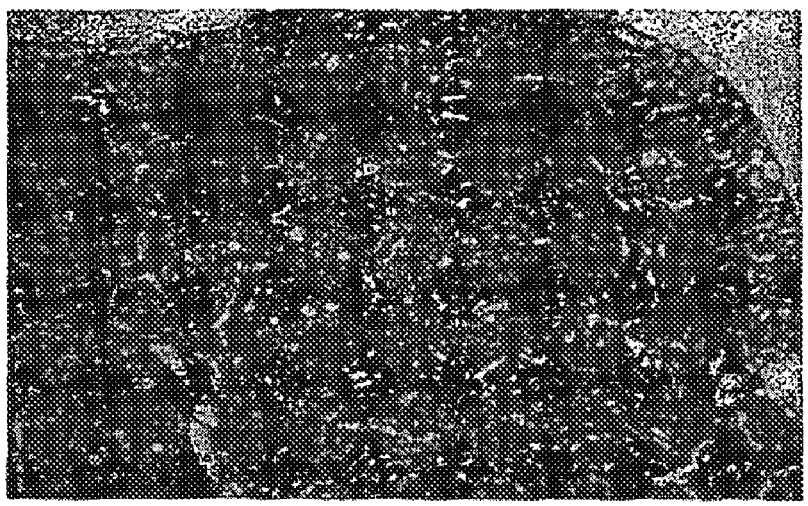
FIG. 3. Panels A-C of this figure are micrographs of renal tissue from rats at 10× magnification. (A) Tissue from sham-operated rat. (B) Tissue from rat in chronic renal failure after 5/6 nephrectomy (Nx control). (C) Tissue from rat treated with OP-1 after 5/6 nephrectomy.
Figure 3B:
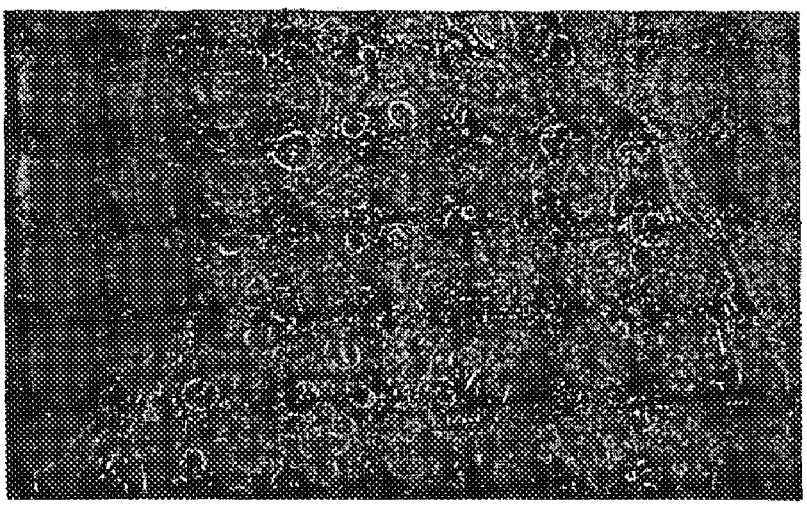
Figure 3A:
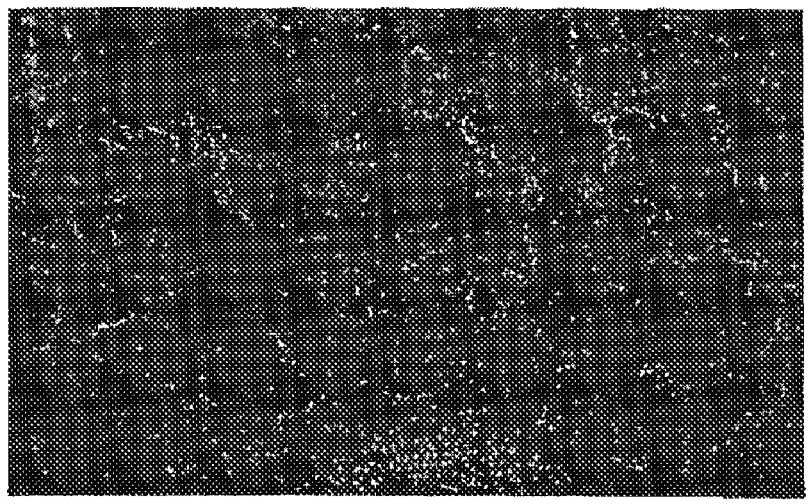
Figure 4C:
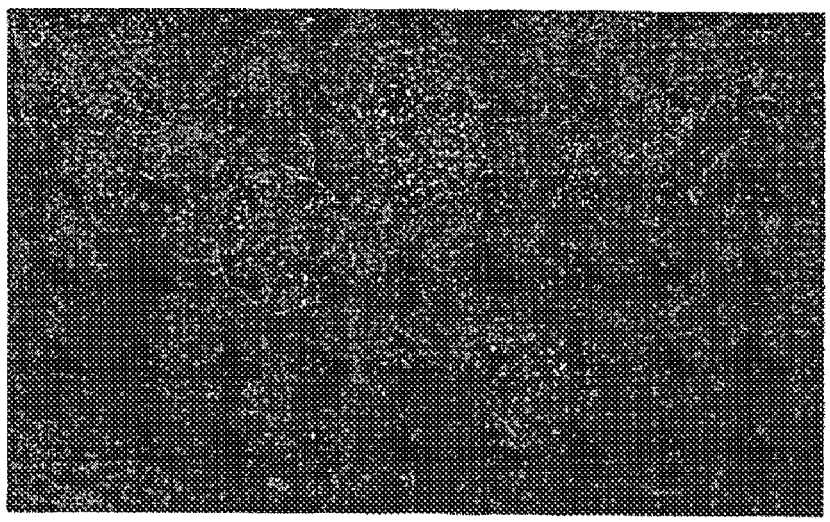
FIG. 4. Panels A-C of this figure are micrographs of renal tissue from rats at 40× magnification. (A) Tissue from sham-operated rat. (B) Tissue from rat in chronic renal failure after 5/6 nephrectomy (Nx control). (C) Tissue from rat treated with OP-1 after 5/6 nephrectomy.
Figure 4B:
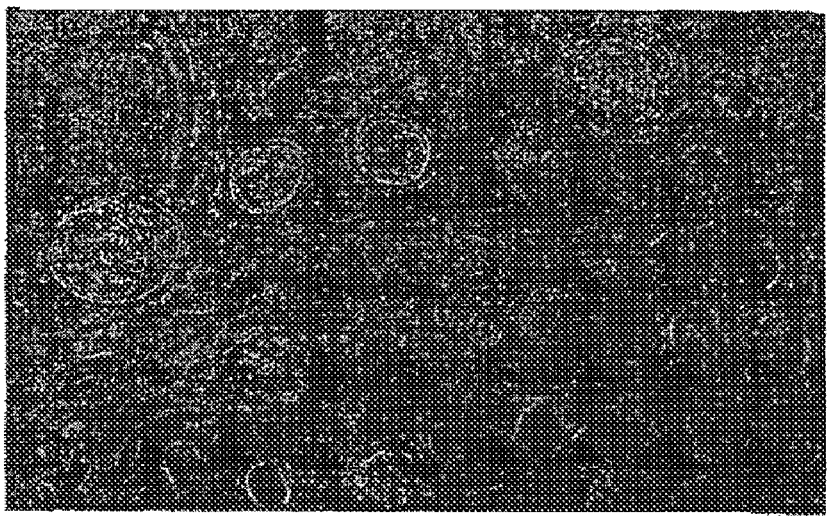
Figure 4A:
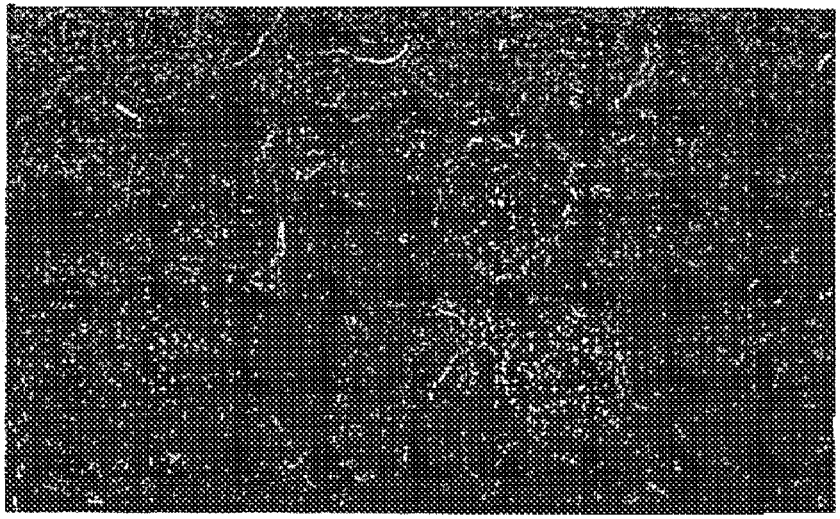

Histological observations indicate that, in contrast to the vehicle treated Nx control group, OP-1 treated nephrectomized rats exhibit relatively normal glomerular histology. FIG. 3, for example, shows typical renal samples from (A) normal rat kidney, (B) untreated Nx control animals, and (C) OP-1 treated nephrectomized rats under low magnification (10×). FIG. 4 shows similar samples under higher magnification (40×). Histomorphometric analysis indicates that OP-1 Nx rats showed reduced incidence of glomerular sclerosis and loop collapse, relatively scattered sclerosis and microaneurysms, and more viable glomeruli compared to Nx control rats (Table 1).

None of the rats died in any group during this study.
Prophylactic Model for Chronic Renal Failure Rats were subjected to partial nephrectomies or sham-operated as described above. In this model, in order to test the ability of OP/BMP renal therapeutic agents to prevent, inhibit or delay the initiation of chronic renal failure, the rats were allowed to recover for approximately two weeks after surgery before initiation of OP-1 therapy. At this point, surviving animals were past the acute renal failure phase and had not yet entered chronic renal failure.

Rats were divided into two groups of 15-20 rats. One group received only vehicle buffer (Nx control) whereas the other received OP-1 treatment at 10 μg/kg body weight given intraperitoneally three times per week. Administration of OP-1 or vehicle continued for a period of approximately 8-9 weeks.

Figure 5:
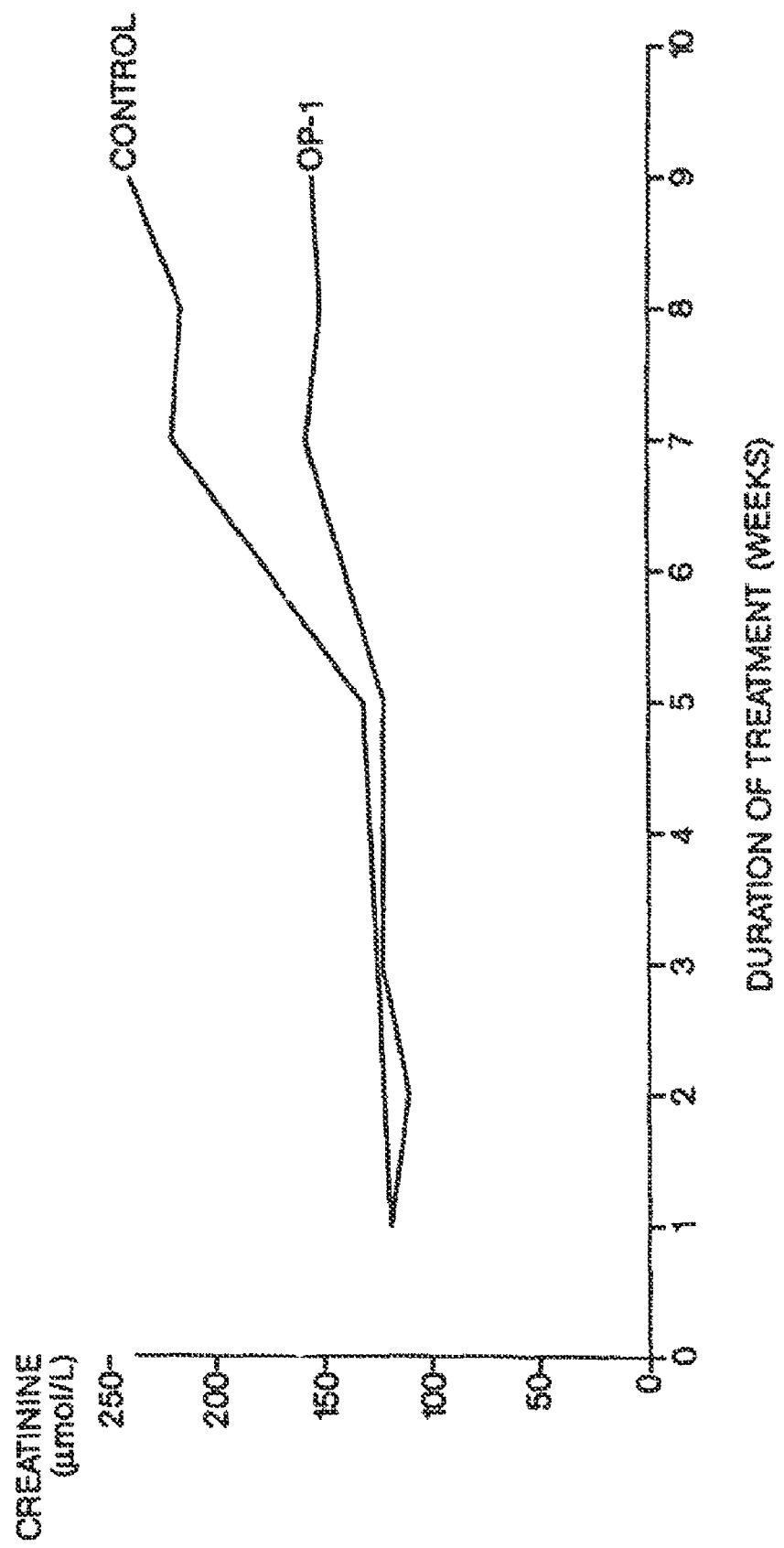
FIG. 5. This figure is a line graph showing average serum creatinine levels over 9 weeks for groups of partially nephrectomized rats. 2-3 weeks post-surgery, rats received injections of vehicle only ("Control") or 10 µg/kg body weight of soluble OP-1 ("OP-1") 3 times per week.

During weeks 1-5 of treatment, both groups showed elevated serum creatinine (>100 μmol/L) relative to sham-operated controls (35±7 μmol/L). At about 5 weeks, both groups began to show a rise in serum creatinine suggesting the onset of progressive or chronic renal fare. The rise in serum creatinine was, however, markedly less rapid in the OP-1 treated group and was significantly lower than in the Nx controls (FIG. 5: $p<0.02$ at weeks 6 and 8; $p<0.01$ at weeks 7 and 9). Similar results were observed in serum BUN values as well.

Figure 6:
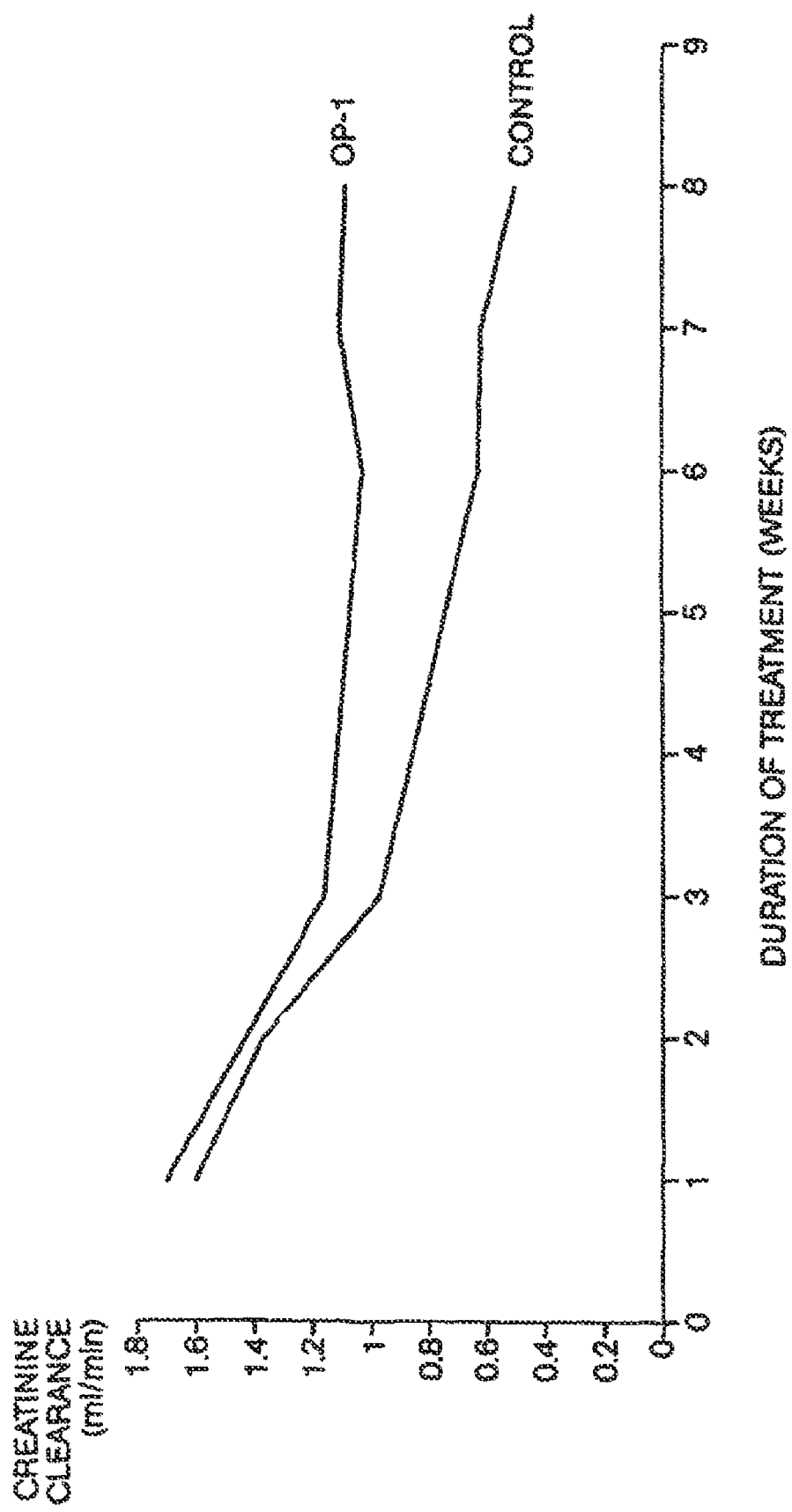
FIG. 6. This figure is a line graph showing average creatinine clearance rates as a measure of GFR over 8 weeks for groups of partially nephrectomized rats. 2-3 weeks post-surgery; rats received injections of vehicle only ("Control") or 10 µg/kg body weight of soluble OP-1 ("OP-1") 3 times per week.

More important, measurements of GFR, based on serum and urine creatinine values, showed a highly significant decrease in both groups of nephrectomized rats (<1.8 ml/min) relative to sham-operated controls (4.7±1.1 ml/min). The GFR in both groups continued to decline during weeks 1-3 of treatment. At approximately three weeks, however, GFR in the OP-1 treated group stabilized whereas the decline in renal function continued in the Nx controls. By week 5, the difference in GFR values between OP-1 treated and Nx control rats had become statistically significant ($p<0.02$). This difference in GFR continued to increase over time ($p<0.01$ at week 6; $p<0.001$ at weeks 7 and 8), as the Nx controls continued to decline but the OP-1 treated rats remained stable (FIG. 6). By the end of 9 weeks, 40% of the Nx control rats were dead whereas none of the OP-1 treated rats had died.

Histological evaluation of tissue sections confirmed that OP-1 treated rats showed greater preservation or maintenance of glomeruli, as well as proximal and distal tubule structures. There were also signs in the OP-1 treated rats of nephrogenic mesenchymal condensations and the appearance of developmental nephrogenic structures. Table 1 reports results of several standard quantitative (e.g., PAS-staining of extracellular matrix) and semi-quantitative (e.g., visual ranking) histomorphometric measures obtained for tissue slices from Nx control and OP-1 treated Nx rats. These results indicate that OP-1 treatment of nephrectomized rates resulted in overall improvement (or reduced degeneration) of kidney tissue morphology, increased mesangial or perivascular thickening, decreased glomerular sclerosis and loop collapse, decreased presence of "scattered" sclerosis and microaneurysms, and an increase in viable glomeruli.

TABLE 1

| Group | Normal Histology | Mesangial Thickening | Glomerular Sclerosis & Loop Collapse | Scattered Sclerosis & Microaneurysms | Absence of Viable Glomeruli |
|---|---|---|---|---|---|
| Control (N = 15) | 2.58 ± 0.22 | 27.3 ± 2.4 | 26.5 ± 3.5 | 34.7 ± 4.2 | 8.9 ± 0.7 |
| OP-1 (N = 20) | 11.41 ± 1.1 | 58.6 ± 3.2 | 14.7 ± 1.3 | 11.8 ± 1.1 | 2.5 ± 0.2 |
| Significance | $p < 0.01$ | $p < 0.01$ | $p < 0.02$ | $p < 0.01$ | $p < 0.01$ |

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A method of treating chronic renal failure in a mammal comprising the step of administering to said mammal a therapeutically effective amount of OP-1.

2. The method of claim 1, wherein said chronic renal failure is associated with renal fibrosis.

3. The method of claim 1, wherein said mammal has less than about 50% of the functional nephron units of a mammal having intact healthy kidneys.

4. The method of claim 1, wherein said mammal has a GFR which is chronically less than about 50% of a GFRexp for said mammal.

5. The method of claim 1, wherein said mammal is a human male weighing at least about 50 kg and has a GFR which is chronically less than about 50ml/min.

6. The method of claim 1, wherein said mammal is a human female weighing at least about 40 kg and has a GFR which is chronically less than about 40ml/min.

7. The method of claim 1, wherein the administration of the bone morphogenic protein is selected from parenteral, intravenous, intraperitoneal, or into the renal capsule.

8. The method of claim 1, wherein the administration of the bone morphogenic protein is by an implanted device.

9. The method of claim 8, wherein a stent has been implanted into the mammal for administration of the bone morphogenic protein.

10. The method of claim 9, wherein the stent is selected from an intravenous stent, an intraperitoneal stent or an intracapsular stent.

* * * * *